United States Patent [19]

Matsumura et al.

[11] Patent Number: 4,533,668

[45] Date of Patent: Aug. 6, 1985

[54] ANTIHYPERGLYCEMIC MORANOLINE DERIVATIVES

[75] Inventors: Shingo Matsumura, Kyoto; Hiroshi Enomoto, Nagaokakyo; Yoshiaki Aoyagi, Kyoto; Yoshiaki Yoshikuni, Kyoto; Kohei Kura, Ohmihachiman; Masahiro Yagi, Kusatsu; Ichiro Shirahase, Kyoto, all of Japan

[73] Assignee: Nippon Shinyaku Co. Ltd., Japan

[21] Appl. No.: 33,839

[22] Filed: Apr. 27, 1979

[30] Foreign Application Priority Data

May 3, 1978 [JP] Japan .................................. 53-53603
Jul. 6, 1978 [JP] Japan .................................. 53-82606
Sep. 29, 1978 [JP] Japan .................................. 53-120661
Jan. 20, 1979 [JP] Japan .................................. 54-5714

[51] Int. Cl.$^3$ .................. A61K 31/445; C07D 211/46
[52] U.S. Cl. ..................................... 514/321; 514/326; 514/328; 546/197; 546/212; 546/213; 546/219; 546/220
[58] Field of Search ............... 542/469, 471, 474, 400; 546/197, 212, 213, 219, 220; 424/267

[56] References Cited

U.S. PATENT DOCUMENTS 4,137,231 1/1979 Murai et al. ...................... 546/242

Primary Examiner—Richard A. Schwartz
Attorney, Agent, or Firm—Jacobs & Jacobs

[57] ABSTRACT

N-aralkylmoranoline and N-aralkenylmoranoline, and their pharmaceutical acceptable non-toxic acid addition salts thereof, pharmaceutical compositions containing the same and methods of inhibiting the increase in blood sugar level by administration of the same.

41 Claims, No Drawings

ANTIHYPERGLYCEMIC MORANOLINE DERIVATIVES

The present invention relates to derivatives of moranoline and to pharmaceutical compositions containing the same.

The present inventors previously isolated for the first time a substance as a naturally occurring substance from a Chinese medicine Mori Cortex, named the same "moranoline" and reported thereon (M. Yagi et al.: Nippon Nogeikagaku Kaishi, 50, 571 (1976). Moranoline is 2-hydroxymethyl, 3,4,5-trihydroxypiperdine.

Subsequent intensive investigation of the pharmacological activity of moranoline by the present inventors revealed that moranoline has a very useful activity for use as a drug, i.e. an activity of inhibiting blood sugar increase in sugar-loaded animals, this finding led them to an invention of a blood sugar increase inhibiting agent containing moranoline, and a patent application was filed (Japanese Kokai No. Sho-52 (1977)-83951).

Thereafter, the present inventors have continued extensive research works on various novel moranoline derivatives synthesized by them and found that certain N-aralkyl or N-aralkenyl derivatives of moranoline have far more potent blood sugar increase inhibiting activity as compared with moranoline, established methods of their synthesis, and completed this invention.

In particular, the present invention now provides an N-substituted moranoline derivative of the formula:

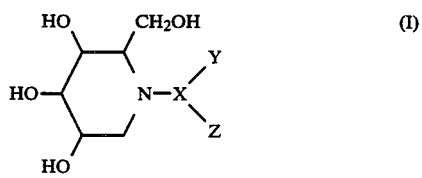 (I)

X is divalent alkyl or alkenyl of 3 to 6 carbon atoms, Y is hydrogen, methyl or

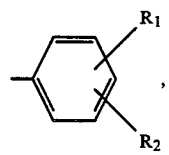, and Z is

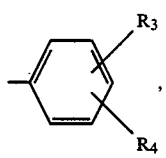,

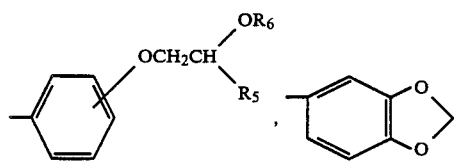

or thienyl, wherein $R_1$, $R_2$, $R_3$ and $R_4$ are independently hydrogen, halogen, lower alkyl, lower alkoxy, hydroxyl, trihalomethyl, phenoxy, dialkylamino, cyano, carboxyl, carbamoyl or carboalkoxy, $R_5$ is hydrogen or hydroxymethyl and $R_6$ is hydrogen, methyl, ethyl or methoxyethyl, and pharmaceutically acceptable non-toxic acid addition salts thereof.

In one embodiment of the invention, the moranline derivative is of the formula:

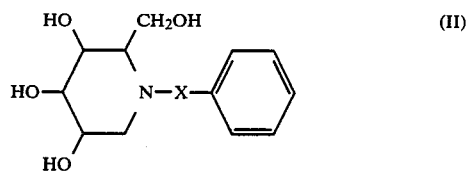 (II)

wherein X is divalent $C_3$ alkyl or $C_3$ alkenyl.

In another embodiment, the moranoline derivative is of the formula:

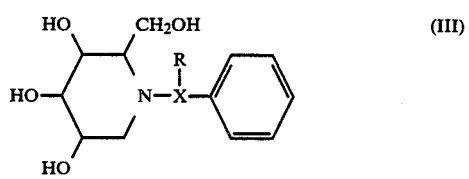 (III)

wherein R is hydrogen or phenyl and X is divalent alkyl or alkenyl of 4 or 5 carbon atoms when R is hydrogen or X is divalent alkenyl of 3, 4 or 5 carbon atoms when R is phenyl.

In another embodiment, the moranoline derivative is of the formula:

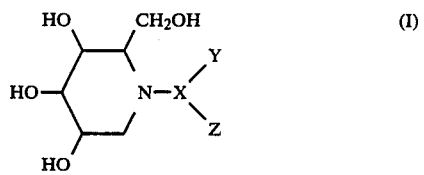 (I)

wherein X is divalent alkyl or alkenyl of 3 to 6 carbon atoms, Y is hydrogen, methyl or

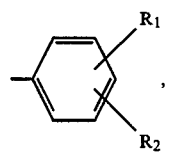

and Z is

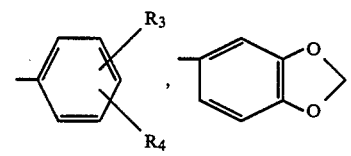

or thienyl.

In another embodiment, the moranoline derivative is of the formula:

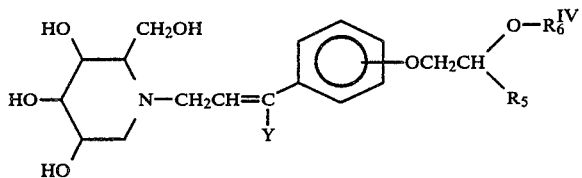

wherein Y is hydrogen or methyl, R₅ is hydrogen or hydroxymethyl and R₆ is hydrogen, methyl, ethyl or methoxyethyl.

As used herein, the term "lower alkyl" shall mean alkyl of 1 to 6 carbon atoms, preferably 1 to 3 carbon atoms. The term "lower alkoxy" shall mean lower alkyl bound to rest of the molecule through an oxygen atom. The term "dialkylamino" shall mean a radical in which each alkyl is lower alkyl. The term "carboalkoxy" shall mean a radical in which the alkoxy moiety is lower alkoxy.

The pharmaceutically acceptable, nontoxic acid addition salts of the compounds of the present invention are preferably the hydrogen halides, especially the hydrochloride and hydrobromide, the phosphate, the nitrate, mono-functional and bifunctional carboxylates and hydroxycarboxylates such as acetate, maleate, succinate, fumarate, tartrate citrate, salicylate, sorbate and lactate and the 1,5-naphthalene disulfonate. The salts are produced by reacting the moranoline compound with the corresponding acid, namely, the hydrogen halide acids such as the hydrochloric acid and hydrobromic acid, phosphoric acid, nitric acid, mono-functional and bifunctional carboxylic acids and hydroxycarboxylic acids such as acetic acid, maleic acid, succinic acid, fumaric acid, tartaric acid, citric acid, salicylic acid, sorbic acid and lactic acid and 1,5-naphthalene disulfonic acid.

The moranoline derivatives of the present invention have a potent blood sugar increase inhibiting activity, and they are very useful for prophylaxis and treatment of hyperglycemic symptoms and various diseases caused by hyperglycemia in humans and animals, such as diabetes, prediabetes, arteriosclerosis, obesity, heart diseases, gastritis, gastric ulcer and duodenal ulcer and other gastrointestinal diseases.

Structurally, the novel moranoline derivatives of the present invention can be characterized as N-aralkylmoranolines or N-aralkenylmoranolines. Their activity is far more potent than that of moranoline itself, as will be described later in detail. Moreover, among N-aralkylmoranolines, N-benzylmoranoline and N-phenethylmoranoline, which are structurally simpler than the compounds of the present invention, are much weaker in activity than the N-aralkylmoranolines of the present invention. Thus, only the substances covered by the present invention, in other words those wherein the chain between the nitrogen atom of moranoline and the phenyl group contains 3 or more carbon atoms, show a very strong activity. N-aralkynylmoranoline derivatives, i.e. those where the chain between the nitrogen atom and the phenyl group contains a triple bond, such as 3-phenyl-2-propynylmoranoline, 3-phenyl-2-butynylmoranoline, 4-phenyl-3-butynylmoranoline, 4-phenyl-3-pentynylmoranoline etc., also show a strong activity, but their value in practice is presently not as great because of difficulty in their commercial production.

Further, there are some compounds that are similarly active among a group of substances which contain in place of the phenyl group, residues of a variety of five- or six-membered, O-, N-, and/or S-containing heterocyclic aromatic rings such as furan, thiophene, pyrrole, imidazole, pyrazole, thiazole, oxazole, pyridine, pyrimidine, pyridazine and pyrazine, or residues of their condensed rings that contain said heterocyclic aromatic rings. Nevertheless, although synthesis of said group of substances is indeed possible by methods analogous to those mentioned in this specification, generally the synthesis is very difficult and is presently not desirable from a commercial standpoint.

The commonest and most advantageous method of synthesis of the compounds of the invention is N-alkylation of moranoline. Thus, they can be synthesized by reacting moranoline with a variety of active aralkylating or aralkenylating agent in the presence of an appropriate deacidifying agent in a polar solvent such as water, an alcohol, DMSO, DMF, a cellosolve, a di- or tri-glyme or dioxane or a mixture thereof or a suspension medium consisting of such polar solvent and a nonpolar solvent such as benzene or hexane. Examples of the active reagent are aralkyl halides, aralkenyl halides, aralkyl sulfonate and aralkenyl phosphates. It is also possible to obtain the contemplated products by using an OH-protected moranoline as a starting material and removing the protective group after the N-substitution reaction. Acetyl, benzoyl, benzyl and tetrahydropyranyl, for example, are suitable protective groups. Further, they can be synthesized also by a so-called reductive alkylation or aralkenylation using as a reagent a carbonyl-containing agent such as an aralkyl- or aralkenylaldehyde. In this case, various kinds of metal complex hydrides as well as catalytic hydrogenation may be employed as means of reduction. The contemplated products can also be obtained by applying said reductive alkylation or aralkenylation to nojirimycin or derivatives thereof and thereby accomplishing the reduction and alkylation or aralkenylation simultaneously. They can also be synthesized by first preparing N-acylmoranoline derivatives and then reducing the same to N-alkyl or N-aralkenyl derivatives, or by some other methods. Moreover, it is possible to derive those compounds that have such a substituent as carboxyl, carbamoyl or carboalkoxy on the aromatic ring from the corresponding nitrile group-containing compounds, e.g. Compound 7, by hydrolysis. In addition, it is possible to convert one of the compounds just mentioned into another one just mentioned, and vice versa. Further, a hydroxyl-containing compound can be converted into the corresponding alkoxy-containing compound and vice versa, as in the case of Compound 30 and Compound 33.

The following examples illustrate the invention.

EXAMPLE 1

Synthesis of N-phenylpropylmoranoline

Moranoline (0.82 g) is dissolved in 2 ml of water and diluted with 6 ml of ethanol, 1.3 g of phenylpropyl bromide and 0.38 g of potassium carbonate are added, and the mixture is heated at 80°–90° C. with stirring for 6 hours, then cooled, diluted with 100 ml of water, washed with ether and passed through an Amberlite IR-120B (H) ion exchange column. The adsorbate is eluted with 1% aqueous ammonia, the eluate evaporated to dryness under reduced pressure, the residue dissolved in isopropyl alcohol, 0.24 g of p-toluenesulfonic acid added, and the resulting crystalline precipitate collected by filtration. This is recrystallized from alcohol to give the contemplated compound. Yield 0.51 g. Melting point 219°–221° C., $[\alpha]_D^{24} = -3.5°$ (water).

EXAMPLE 2

Synthesis of N-cinnamylmoranoline

Moranoline (3.2 g) is dissolved in 100 ml of DMF, 7.9 g of cinnamyl bromide and 8.0 g of anhydrous potassium carbonate are added, and the mixture is heated at 70°–80° C. with stirring for 4 hours, then cooled, diluted with 400 ml of water, made acid with hydrochloric acid, and washed with benzene. The benzene layer is extracted with 1% hydrochloric acid, the combined aqueous layers are made alkaline with ammonia, and extracted with n-butanol. The extract is washed with water and evaporated to dryness under reduced pressure. The remaining crystals are recrystallized from methanol. Yield 2.8 g. Melting point 167°–168° C. $[\alpha]_D^{24} = -49.0°$ (methanol).

The hydrochloride: recrystallized from methanol, m.p. 216°–218° C. $[\alpha]_D^{24} = -15.0°$ (water).

The activity of the compounds of Examples 1 and 2 were determined by administering 10 mg/kg of each compound orally to rats together with 2 g/kg of sucrose and comparing the blood sugar increase one hour later with that of a control group receiving only the sucrose. The inhibition rate was 54% for the compound of Example 1 and 93% for the compound of Example 2. Thus it has been revealed that they have far more potent activity when compared with the inhibition rate of 28% shown by moranoline under the same test conditions.

Using the conditions set forth above, other compounds of the invention were tested with the results set forth in Tables 1 and 2 below.

TABLE 1

| Compound No. | XYZ | % Inhibition |
|---|---|---|
| [I] | 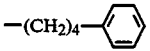 | 127 |
| [II] | 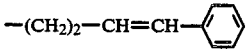 | 98 |
| [III] | 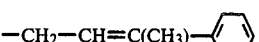 | 108 |
| [IV] | 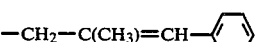 | 90 |
| [V] |  | 98 |
| [VI] |  | 103 |
| [VII] |  | 117 |
| [VIII] |  | 94 |
| [IX] |  | 117 |
| [X] |  | 98 |
| [XI] |  | 95 |

TABLE 2

| Compound No. | X Y Z | % Inhibition | m.p. (°C.) | $[\alpha]_D^{24}$ |
|---|---|---|---|---|
| 1 | 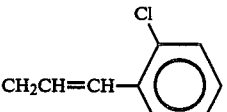 | 122 | 117–179 | −29.3° (methanol) |
| 2 | 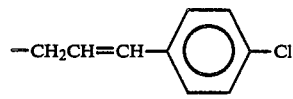 | 72 | 225–228 | −43.6° (methanol) |
| 3 | 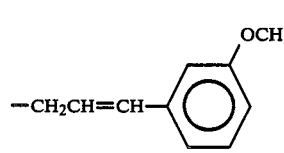 | 118 | 167–169 | −50.1° (methanol) |

TABLE 2-continued
Compounds of Formula I

| Compound No. | X Y Z | % Inhibition | m.p. (°C.) | $[\alpha]_D^{24}$ |
|---|---|---|---|---|
| 4 | —CH$_2$CH=CH—C$_6$H$_4$—CH$_3$ | 100 | 181–184 | −48.9° (methanol) |
| 5 | —CH$_2$CH=CH—(2-CH$_3$-C$_6$H$_4$) | 107 | 157–160 | −45.7° (methanol) |
| 6 | —CH$_2$CH=CH—(3,4-methylenedioxy-C$_6$H$_3$) | 98 | 187–190 | −49.6° (methanol) |
| 7 | —CH$_2$CH=CH—C$_6$H$_4$—CN | 108 | 171–172 | −50.9° (methanol) |
| 8 | —CH$_2$CH=CH—C$_6$H$_4$—CO$_2$H | 100 | hydrochloride 258–262 (decomposition) | −17.8° (water) |
| 9 | —CH$_2$CH=CH—C$_6$H$_4$—CONH$_2$ | 102 | 218–220 | −3.7° (acetic acid) |
| 10 | —CH$_2$CH=CH—C$_6$H$_4$—CO$_2$CH$_3$ | 97 | hydrochloride 197–199 | −12.3° (methanol) |
| 11 | —CH$_2$CH=C(CH$_3$)—(3-Cl-C$_6$H$_4$) | 100 | 145–147 | −41.6° (methanol) |
| 12 | —CH$_2$CH=C(CH$_3$)—(4-Cl-C$_6$H$_4$) | 127 | 174–175 | −43.7° (methanol) |
| 13 | —CH$_2$CH=C(CH$_3$)—(4-Br-C$_6$H$_4$) | 99 | 184–186 | −32.0° (methanol) |
| 14 | —CH$_2$CH=C(CH$_3$)—(3,4-Cl$_2$-C$_6$H$_3$) | 100 | 162–164 | −37.6° (methanol) |

TABLE 2-continued

Compounds of Formula I

| Compound No. | X Y Z | % Inhibition | m.p. (°C.) | $[\alpha]_D^{24}$ |
|---|---|---|---|---|
| 15 | −CH₂CH=C(CH₃)−(3-OCH₃-C₆H₄) | 113 | 159–161 | −39.6° (methanol) |
| 16 | −CH₂CH=C(CH₃)−(4-OCH₃-C₆H₄) | 105 | 177–179 | −60.8° (methanol) |
| 17 | −CH₂CH=C(CH₃)−(4-CH₃-C₆H₄) | 111 | 166–169 | −45.6° (methanol) |
| 18 | −CH₂CH₂CH=CH−(4-Cl-C₆H₄) | 70 | 162–165 | −25.8° (methanol) |
| 19 | −CH₂CH₂CH=CH−(4-F-C₆H₄) | 65 | 168–172 | −23.8° (methanol) |
| 20 | −CH₂CH₂CH=CH−(4-CH₃-3-F-C₆H₃) | 78 | 161–163 | −22.7° (methanol) |
| 21 | −CH₂CH₂CH=CH−(4-OCH₃-3-Cl-C₆H₃) | 84 | 173–175 | −20.2° (methanol) |
| 22 | −CH₂CH₂CH=CH−(4-OC₂H₅-3-F-C₆H₃) | 89 | 189–193 | −21.3° (DMSO) |
| 23 | −CH₂CH₂CH=C(CH₃)−(2-Cl-C₆H₄) | 51 | hydrate 72–76 | −13.4° (methanol) |
| 24 | −CH₂CH₂CH=C(CH₃)−(3-Cl-C₆H₄) | 73 | 129–133 | −22.8° (methanol) |
| 25 | −CH₂CH₂CH=C(CH₃)−(4-Cl-C₆H₄) | 80 | 160–163 | −24.7° (methanol) |

TABLE 2-continued
Compounds of Formula I

| Compound No. | X Y Z | % Inhibition | m.p. (°C.) | $[\alpha]_D^{24}$ |
|---|---|---|---|---|
| 26 | —CH$_2$CH$_2$CH=C(CH$_3$)—(3-F-phenyl) | 106 | 146–150 | −24.0° (methanol) |
| 27 | —CH$_2$CH$_2$CH=C(CH$_3$)—(4-F-phenyl) | 93 | 145–148 | −21.7° (methanol) |
| 28 | —CH$_2$CH$_2$CH=C(CH$_3$)—(3-CF$_3$-phenyl) | 36 | 140–144 | −22.7° (methanol) |
| 29 | —CH$_2$CH$_2$CH=C(CH$_3$)—(2-CH$_3$O-phenyl) | 83 | hydrate 56–60 | −13.9° (methanol) |
| 30 | —CH$_2$CH$_2$CH=C(CH$_3$)—(4-OCH$_3$-phenyl) | 102 | 152–156 | −32.8° (ethanol) |
| 31 | —CH$_2$CH$_2$CH=C(CH$_3$)—(4-OC$_2$H$_5$-phenyl) | 109 | 147–151 | −18.6° (methanol) |
| 32 | —CH$_2$CH$_2$CH=C(CH$_3$)—(4-phenoxyphenyl) | 75 | hydrate 85–90 | −17.2° (methanol) |
| 33 | —CH$_2$CH$_2$CH=C(CH$_3$)—(4-OH-phenyl) | 77 | 169–173 | −18.8° (methanol) |
| 34 | —CH$_2$CH$_2$CH=C(CH$_3$)—(4-N(CH$_3$)$_2$-phenyl) | 103 | 176–181 | −26.2° (methanol) |
| 35 | —CH$_2$CH$_2$CH=C(CH$_3$)—(2-CH$_3$-phenyl) | 73 | 124–127 | −19.7° (methanol) |

TABLE 2-continued

Compounds of Formula I

| Compound No. | X Y Z | % Inhibition | m.p. (°C.) | $[\alpha]_D^{24}$ |
|---|---|---|---|---|
| 36 | —CH$_2$CH$_2$CH=C(CH$_3$)(2,4,5-trimethyl-diisopropyl-phenyl) [structure: —CH₂CH₂CH=C with CH₃ group and phenyl ring bearing CH₃, CH₃, and CH(CH₃)₂ substituents] | 54 | hydrate 48–52 | −16.4° (methanol) |
| 37 | —CH$_2$CH=C(phenyl)(4-chlorophenyl) | 30 | hydrate 99–100 | −59.5° (methanol) |
| 38 | —CH$_2$CH=C(phenyl)(4-fluorophenyl) | 22 | 145–147 | −58.5° (methanol) |
| 39 | —CH$_2$CH=C(phenyl)(4-methoxyphenyl) | 70 | amorphous powder | −44.3° (methanol) |
| 40 | —CH$_2$CH$_2$CH=C(4-chlorophenyl)(4-chlorophenyl) | 50 | ethylene glycol adduct 102–105 | −11.7° (methanol) |
| 41 | —CH$_2$CH$_2$CH=C(2-methoxyphenyl)(2-methoxyphenyl) | 68 | 167–169 | −9.6° (methanol) |
| 42 | —CH$_2$CH$_2$CH=C(4-methoxyphenyl)(4-methoxyphenyl) | 75 | hydrate 90–94 | −19.0° (DMSO) |

TABLE 2-continued

Compounds of Formula I

| Compound No. | X Y Z | % Inhibition | m.p. (°C.) | $[\alpha]_D^{24}$ |
|---|---|---|---|---|
| 43 | 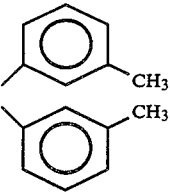 —CH$_2$CH$_2$CH=C(C$_6$H$_4$-CH$_3$)(C$_6$H$_4$-CH$_3$) | 45 | hydrate 78–80 | −14.5° (methanol) |
| 44 | 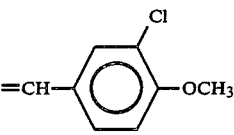 —CH$_2$CH$_2$CH$_2$CH=CH—(3-Cl,4-OCH$_3$-C$_6$H$_3$) | 94 | 111–115 | −14.6° (methanol) |
| 45 | 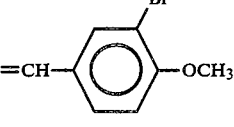 —CH$_2$CH$_2$CH$_2$CH=CH—(3-Br,4-OCH$_3$-C$_6$H$_3$) | 84 | 115–117 | −17.3° (methanol) |
| 46 | 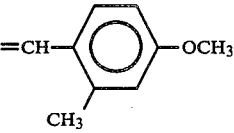 —CH$_2$CH$_2$CH$_2$CH=CH—(4-OCH$_3$,3-CH$_3$-C$_6$H$_3$) | 97 | hydrate 71–74 | −12.1° (methanol) |
| 47 | 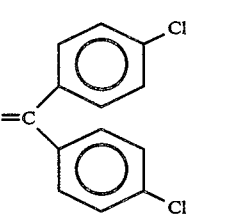 —CH$_2$CH$_2$CH$_2$CH=C(4-Cl-C$_6$H$_4$)(4-Cl-C$_6$H$_4$) | 24 | 127–130 | −13.6° (methanol) |
| 48 | 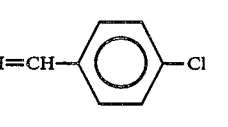 —CH$_2$CH=C(CH$_3$)—CH=CH—(4-Cl-C$_6$H$_4$) | 85 | 180–183 | −27.2° (pyridine) |
| 49 | 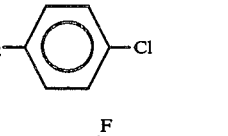 —CH$_2$CH$_2$CH$_2$CH$_2$—(4-Cl-C$_6$H$_4$) | 101 | 128–130 | −18.0° (methanol) |
| 50 | 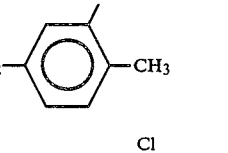 —CH$_2$CH$_2$CH$_2$CH$_2$—(3-F,4-CH$_3$-C$_6$H$_3$) | 114 | 125–127 | −17.0° (methanol) |
| 51 | 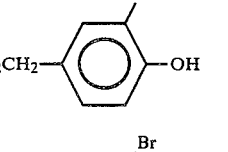 —CH$_2$CH$_2$CH$_2$CH$_2$CH$_2$—(3-Cl,4-OH-C$_6$H$_3$) | 78 | hydrate 70–75 | −13.1° (methanol) |
| 52 | 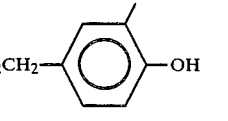 —CH$_2$CH$_2$CH$_2$CH$_2$CH$_2$—(3-Br,4-OH-C$_6$H$_3$) | 72 | 143–146 | −10.8° (methanol) |

TABLE 2-continued

Compounds of Formula I

| Compound No. | X Y Z | % Inhibition | m.p. (°C.) | $[\alpha]_D^{24}$ |
|---|---|---|---|---|
| 53 | —CH$_2$CH$_2$CH$_2$CH(3,4-dimethoxyphenyl) 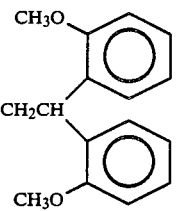 | 107 | 184–186 | −15.1° (DMSO) |
| 54 | —CH$_2$CH=CH—(2-thienyl) 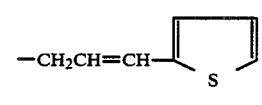 | 99 | 159–162 | −57.5° (methanol) |
| 55 | —CH$_2$CH=C(CH$_3$)—(2-thienyl) 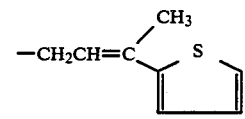 | 101 | 181–183 | −55.3° (methanol) |

All of the compounds of Table 1 show approximately 100% or more inhibition. In contrast, the inhibition rate for moranoline under the same test conditions was only 28%, and N-benzyl-moranoline and N-phenethyl-moranoline actually potentiated blood sugar increase by 35% and 21%, respectively.

Likewise, the compounds of Table 2 also have a far more potent blood-sugar-increase inhibiting activity as compared with moranoline. Exceptionally, only a few compounds, which are sparingly soluble in water, are active only to approximately the same degree as moranoline. There also can be found some compounds that show similar activity as shown by the compounds of the present invention among compounds which have the same carbon skeleton as that of the compounds of the present invention and contain a triple bond as an unsaturated bond in the carbon chain and among compounds which have aromatic rings other than the phenyl or thiophene ring, such as naphthyl, O-, N- or S-containing, five- or six-membered, heterocyclic aromatic groups, e.g. furan, pyrrole, imidazole, pyrazole, oxazole, thiazole, pyridine, pyrimidine, pyridazine and pyrazine residue, or condensed ring groups comprising said heterocyclic groups, e.g. benzofuran, indole, benzothiophene, quinoline and purine residue. Also, some effective substances can be found among compounds wherein said condensed ring has been converted to such a skeleton as carbostyril, isocarbostyril, indane, coumarine, isocoumarine and benzopyrone. Thus, it seems that the blood sugar increase inhibiting activity possessed by the compounds covered by the present increase is an activity generally recognizable in the group of compounds similar in structure to the compounds of the present invention, without being essentially influenced by certain changes in the kind of aromatic ring, kind of the substituent on the aromatic ring, structure of the hydrocarbon residue, etc. Nevertheless, the number of carbon atoms in the hydrocarbon residue and especially the number of carbon atoms in the main chain which is determinant of the distance between the nitrogen atom of moranoline and the aromatic have great influence upon the activity. If the chain length is beyond the limits, specified by the present category, i.e. 3–6 carbon atoms, the activity will be much lower and some compounds will even potentiate blood sugar increase.

Those compounds of Table 2 that have inhibition rates of 20–30% are all only sparingly water soluble, which fact appears to be one of the causes of the low activity found in that experiment. Even those compounds which show relatively low activity are almost equally or more active than moranoline itself which shows an inhibition rate of 28% under the same test conditions. Two examples of compounds which are outside the scope of the present invention and have carbon chain, X, beyond the limits of 3–6 carbon atoms, namely N-phenethylmoranoline and N-benzylmoranoline, potentiated blood sugar increase by 21% and 35%, respectively, and another example of such compounds, N-(8-phenyloctyl)moranoline showed a very low activity, that is an inhibition rate of 11%.

Table 3 below sets forth activity data for those compounds of the invention of formula IV, which are N-cinnamylmoranoline derivatives. In such compounds, the activity is dependent on the number of carbon atoms contained in the carbon chain between the aromatic ring and the nitrogen atom of moranoline. When the chain is of 1 or 2 carbon atoms, no activity can be found at all, but when the chain contains 3 or more carbon atoms, the activity is found. Especially when the chain contains 3 or 4 carbon atoms, the activity is maximal, and particularly the activity of N-cinnamylmoraline is very strong.

Further, those derivatives that have a substituent at the γ-position of the cinnamyl group, such as γ-methylcinnamyl and γ-ethylcinnamyl derivatives, are as active as the cinnamyl derivative. Generally, those derivatives that have as substituent a variety of alkoxy groups on the aromatic nucleus are highly active. Among others, the compounds having a glycol ether type substituent and covered by the present invention, are highly active and of low toxicity, and especially useful as drugs. The cinnamyl derivatives having said glycol ether type substituent include, in addition to the substances covered by the present invention, those cinnamyl derivatives that have an ethoxy or propoxy group substituted by a variety of alkoxy groups of 1 to 18 carbon atoms. They may have two or more of said glycol ether type substituents, and of course, there may be present a number of isomers depending on the position of substitution. The useful physiological activity possessed by the substances covered by the present invention is a property common to said glycol ether type cinnamylmoranoline derivatives in general, but not limited to the substances covered by the present invention.

All of the substituted cinnamylmoranoline derivatives covered by the present invention not only have very potent activity as compared with moranoline but also have much more potent activity than N-alkylmoranolines, or unsubstituted cinnamylmoranolines.

Table 3 sets forth the activity of typical examples of substituted cinnamylmoranoline derivatives as compared with that of N-benzylmoranoline, N-phenethylmoranoline, N-cinnamylmoranoline (Example 2) as well as moranoline and N-methylmoranoline. The activity is shown in terms of % inhibition obtained by comparing the blood sugar increase 120 minutes after the oral administration of 1 mg/kg of the test substance together with 2 g/kg of sucrose to rats with that found in the control group receiving only the sucrose.

TABLE 3

| Compound No. | Compounds of Formula I X Y Z | Inhibition rate |
|---|---|---|
| 55 | $-CH_2CH=CH-$⟨phenyl with $OCH_2CH_2OCH_3$⟩ | 128% |
| 56 | $-CH_2CH=C(CH_3)-$⟨phenyl with $OCH_2CH_2OCH_3$⟩ | 106% |
| 57 | $-CH_2CH=CH-$⟨phenyl⟩$-OCH_2CH_2OCH_3$ | 80% |
| 58 | $-CH_2CH=CH-$⟨phenyl⟩$-OCH_2CH_2OC_2H_5$ | 93% |
| 59 | $-CH_2CH=CH-$⟨phenyl⟩$-OCH_2CH_2OH$ | 90% |
| 60 | $-CH_2CH=CH-$⟨phenyl⟩$-OCH_2CH_2OCH_2CH_2OCH_3$ | 126% |
| 61 | $-CH_2CH=CH-$⟨phenyl⟩$-OCH_2CH(CH_2OH)(OH)$ | 91% |
| Moranoline | H | 41% |
| N—Methylmoranoline | $-CH_3$ | 33% |
| N—Benzylmoranoline | $-CH_2-$⟨phenyl⟩ | −12.1% |
| N—Phenethylmoranoline | $-CH_2CH_2-$⟨phenyl⟩ | −3.6% |
| N—Cinnamylmoranoline (Example 2) | $-CH_2CH=CH-$⟨phenyl⟩ | 51% |

The pharmaceutical compositions of the present invention contain a major or minor amount e.g. 0.1% to 99.5%, preferably 0.5% to 90% of active ingredient as above defined in combination with a pharmaceutically acceptable, nontoxic, inert diluent or carrier, the carrier comprising one or more solid semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be: from 0.01 to 300 mg of the moranoline derivative of the present invention, preferably 0.01 to 50 mg, per Kg of body weight per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

While the routes of administration include oral, parenteral (i.e., intramuscular, intraperitoneal and intravenous), and rectal, oral administration is particularly preferred.

The preferred pharmaceutical compositions are therefore those in a form suitable for oral administration such as tablets and suspensions.

The Examples that folow illustrate the preparation of representative compounds illustrated in Tables 1-3 above. All of the compounds of the invention can be prepared in an analogous manner.

EXAMPLE 3

Synthesis of Compound I

Moranoline (3.26 g) is dissolved in a mixture of 25 ml of methanol and 25 ml of DMF with heating, 5.0 g of sodium bicarbonate and 8.5 g of 4-phenylbutyl bromide are added, and the mixture is heated and stirred at 80° C. for 4 hours and then at 95° C. for 2 hours. The reaction mixture is diluted with water, acidified by addition of hydrochloric acid, washed with benzene, made alkaline with ammonia and extracted with n-butanol. After washing with water, the butanol is distilled off. The remaining crystals are recrystallized from acetone. Melting point 118°–119° C. Yield 2.91 g. $[\alpha]_D^{24} = -19.0°$ (methanol).

The p-toluenesulfonate salt: recrystallized from isopropyl alcohol. Melting point 163°–164° C., $[\alpha]_D^{24} = -4°$ (water).

EXAMPLE 4

Synthesis of Compound II

Moranoline (3.26 g) is dissolved in 25 ml of DMF with heating, 4.0 g of sodium hydrogen carbonate and 7.0 g of 4-phenyl-3-butenyl bromide are added and the mixture is heated at 80°–85° C. with stirring for 6 hours. The reaction mixture is treated as in Example 1, and 3.5 g of p-toluenesulfonic acid is added to the reaction product so obtained to convert the same into the salt, which is recrystallized from ethanol. Melting point 160°–162° C., $[\alpha]_D^{24} = -8.0°$ (methanol). Yield 3.12 g.

EXAMPLE 5

Synthesis of Compound V

Moranoline (1.5 g) is dissolved in 20 ml of DMF with heating 1.5 g of potassium carbonate and 4.0 g of γ-phenylcinnamyl bromide are added and the mixture is heated at 60° for an hour with stirring. Thereafter, the reaction product is recovered by the procedure of Example 1 and recrystallized from a mixture of ethyl acetate and n-hexane. Melting point 91°–94° C., $[\alpha]_D^{24} = -57.2°$ (methanol). Yield 0.93 g.

EXAMPLE 6

Synthesis of Compound XI

Moranoline (2.0 g) is dissolved in 40 ml of DMF with heating, 3.5 g of potassium carbonate and 5.5 g of 4-phenyl-3-pentenyl bromide are added and the mixture is heated at 60° for 11 hours with stirring. Thereafter, the reaction product is recovered by the procedure of Example 1 and recrystallized from isopropyl alcohol. Melting point 126°–131° C. $[\alpha]_D^{24} = -23.2°$ (methanol). Yield 0.40 g.

In the following are shown physical characteristics of other compounds covered by the present invention than those mentioned above. These have been synthesized according to the above process.

Compound III Melting point: 169°–170° C., $[\alpha]_D^{24} = -39.9°$ (methanol)
Compound IV Melting point: 138°–141° C., $[\alpha]_D^{24} = -71.4°$ (methanol)
Compound VI Melting point: 164°–166° C., $[\alpha]_D^{24} = -16.9°$ (methanol)
Compound VII Melting point: 160°–162° C., $[\alpha]_D^{24} = -10.4°$ (methanol)
Compound VIII (p-toluenesulfonate) Melting point: 190°–192° C., $[\alpha]_D^{24} = -2.7°$ (water)
Compound IX Melting point: 116°–118° C., $[\alpha]_D^{24} = -51.7°$ (methanol)
Compound X (p-toluenesulfonate) Melting point: 223°–226° C. $[\alpha]_D^{24} = -4.6°$ (methanol)

EXAMPLE 7

Synthesis of Compound 5 m-Methylcinnamyl bromide (2.0 g) (obtained by treatment with concentrated hydrobromic acid of 1-(m-methylphenyl)allyl alcohol prepared in turn from m- methylbenzaldehyde and vinyl magnesium bromide), 1.0 g of moranoline and 3.0 g of sodium hydrogen carbonate are stirred in 15 ml of ethylene glycol at 40°–55° C. for 1.5 hours. After completion of the reaction, the reaction mixture is diluted with 100 ml of water, and acidified with hydrochloric acid. The neutral substance is removed by extraction with ether. The aqueous layer is made alkaline with ammonia and extracted with n-butanol. The extract is purified by silica gel column chromatography using chloroform-methanol (3:1), and recrystallized from isopropyl alcohol. Yield 0.65 g. Melting point 157°–160° C. $[\alpha]_D^{24} = -45.7°$ (methanol).

EXAMPLE 8

Synthesis of Compounds 8 and 9

Compound 7 (0.5 g) prepared in the same manner as for Compound 5 (Example 8) is allowed to stand in 30 ml of concentrated hydrochloric acid at room temperature overnight. The reaction mixture is evaporated to dryness under reduced pressure, and the residue dissolved in 5 ml of water and the solution made alkaline with ammonia. The resulting crystalline precipitate is recrystallized from aqueous methanol. Yield 0.29 g. Melting point 218°–220° C. $[\alpha]_D^{24} = -3.7°$ (acetic acid).

Compound 7 (1.8 g) is heated in 70 ml of concentrated hydrochloric acid at 95°–100° for 3 hours, and the reaction mixture concentrated to about 20 ml under reduced pressure. The precipitate which forms on cooling is collected by filtration and recrystallized from methanol. Yield 1.42 g. Melting point 258°–262° C. (decomposition). $[\alpha]_D^{24} = -17.8°$ (water).

EXAMPLE 9

Synthesis of Compound 12

The crude reaction product obtained by stirring 5.0 g of the carbinol compound (prepared from p-chloroacetophenone and vinyl magnesium bromide with 30 ml of concentrated hydrobromic acid for an hour is stirred with 1.5 g of moranoline and 4.0 g of sodium hydrogen carbonate in 15 ml of ethylene glycol at 60°–70° C. for 2 hours. The same treatment as in Example 8 followed by recrystallization of the reaction product from isopropyl alcohol gives a yield of 1.1 g. Melting point 174°–175° C. $[\alpha]_D^{24} = -43.7°$ (methanol).

EXAMPLE 10

Synthesis of Compound 21

4-(3-Chloro-4-methoxyphenyl)-3-butenyl bromide is prepared by stirring 4.0 g of 1-(3-chloro-4-methoxyphenyl)-1,3-butanediol (obtainable from o-chloroanisole and succinic anhydride by Friedel-Craft reaction followed by esterification and reduction with lithium aluminum hydride) and 4.0 g of phosphorus tribromide in 40 ml of benzene at 0°–5° C. for 5 hours followed by stirring at room temperature for 12 hours. The bromide (2.7 g), 1.3 g of moranoline and 4.5 g of potassium carbonate are stirred in 50 ml of DMF at 70°–80° C. for 14 hours. The reaction product recovered by the procedure of Example 7 is recrystallized from methanol. Yield 0.6 g. Melting point 173°–175° C. $[\alpha]_D^{24} = -20.2°$ (methanol).

EXAMPLE 11

Synthesis of Compounds 30 and 33

The carbinol compound (14 g) obtained by Grignard reaction of cyclopropyl methyl ketone and p-methoxy magnesium bromide is stirred with 40 ml of concentrated hydrobromic acid at room temperature for an hour, and the reaction product stirred together with 3.0 g of moranoline and 15 g of potassium carbonate in 80 ml of DMF at 60°–70° C. for 5 hours. The reaction product recovered by the procedure of Example 1 is recrystallized from isopropyl alcohol. Yield 1.9 g. Melting point 152°–156° C. $[\alpha]_D^{24} = -32.8°$ (ethanol).

Compound 30 (0.7 g) is heated with 10 g of pyridine hydrochloride at 200° C. for 30 minutes. The reaction product is recovered by the procedure of Example 1 and recrystallized from isopropyl alcohol. Yield 0.35 g. Melting point 169°–173° C. $[\alpha]_D^{24} = -18.8°$ (methanol).

EXAMPLE 12

Synthesis of Compound 38

The carbinol compound (5.0 g) prepared from 4-fluorobenzophenone and vinyl magnesium bromide by Grignard reaction is stirred with 25 ml of concentrated hydrobromic acid at room temperature for an hour. The reaction product together with 1.5 g of moranoline and 5.0 g of sodium hydrogen carbonate is stirred in 15 ml of ethylene glycol at 60°–70° C. for 6 hours. The reaction product is recovered by the procedure of Example 1 and recrystallized from ethyl acetate. Yield 1.75 g. Melting point 145°–147° C. $[\alpha]_D^{24} = -58.5°$ (methanol).

EXAMPLE 13

Synthesis of Compound 41

The carbinol compound (13 g) prepared from ethyl cyclopropanecarboxylate and o-methoxyphenyl magnesium bromide is stirred with 50 ml of concentrated hydrobromic acid at room temperature for 2 hours. The reaction product obtained (10 g) is stirred with 2.5 g of moranoline and 6.0 g of potassium carbonate in 60 ml of DMF at 65° for 14 hours. The reaction product is recovered by the procedure of Example 1 and recrystallized from isopropyl alcohol. Yield 4.1 g. Melting point 167°–169° C. $[\alpha]_D^{24} = -9.6°$ (methanol).

EXAMPLE 14

Synthesis of Compound 44

1-(3-Chloro-4-methoxyphenyl)-1,5-pentanediol synthesized from o-chloroanisole and glutaric anhydride by the same procedure as employed for Compound 21 is reacted with triphenylphosphine and carbon tetrabromide in acetonitrile. The resulting bromine derivative (6.0 g) is stirred with 1.0 g of moranoline and 5.0 g of potassium carbonate in 30 ml of ethylene glycol at 60°–70° for 5 hours. The reaction product is recovered by the procedure of Example 1 and recrystallized from water. Yield 0.50 g. Melting point 111°–115° C. $[\alpha]_D^{24} = -14.6°$.

EXAMPLE 15

Synthesis of Compound 47

The reaction product obtained by refluxing with 30 ml of concentrated hydrobromic acid for an hour 5.0 g of the carbinol compound prepared from δ-valerolactone and p-chlorophenyl magnesium bromide is stirred with 1.0 g of moranoline and 5.0 g of sodium hydrogen carbonate in a mixture of 10 ml of ethylene glycol and 10 ml of DMF at 85° C. for 4.5 hours. The reaction product is recovered by the procedure of Example 7 and recrystallized from isopropyl alcohol. Yield 0.26 g. Melting point 127°–130° C. $[\alpha]_D^{24} = -13.6°$ (methanol).

EXAMPLE 16

Synthesis of Compound 48

The carbinol compound (5.0 g) prepared from p-chlorobenzalacetone and vinyl magnesium bromide is stirred with 25 ml of concentrated hydrobromic acid at 3°–5° C. for 45 minutes, and the reaction product stirred with 1.0 g of moranoline and 5.0 g of sodium hydrogen carbonate in 10 ml of ethylene glycol at 60°–70° C. for 2 hours. The reaction product is recovered by the procedure of Example 1 and recrystallized from ethanol. Yield 0.35 g. Melting point 180°–183° C. $[\alpha]_D^{24} = -27.4°$ (pyridine).

EXAMPLE 17

Synthesis of Compound 54

The carbinol compound (5.0 g) prepared from thiophene-2-aldehyde and vinyl magnesium bromide is dissolved in 50 ml of chloroform, 4.1 g of moranoline added, and 3.6 g of methanesulfonyl chloride dropped over 10 minutes with ice cooling. After stirring at 0°–10° C. for 0.5 hour, the reaction mixture is washed with water and dried, and the solvent distilled off under reduced pressure. The remaining reaction product is stirred with 1.0 g of moranoline and 5.0 g of sodium hydrogen carbonate in 10 ml of ethylene glycol at 55°–65° C. for 2 hours. The reaction product is recovered by the procedure of Example 7 and recrystallized from isopropyl alcohol. Yield 0.15 g. Melting point 159°–162° C. $[\alpha]_D^{24} = -57.5°$ (methanol).

EXAMPLE 18

Synthesis of Compound 55

A solution of 12.7 g of m-β-methoxyethoxybenzaldehyde (prepared by reaction of m-hydroxybenzaldehyde with methoxyethyl bromide in DMF in the presence of anhydrous potassium carbonate) in 50 ml of anhydrous tetrahydrofuran is dropped into an anhydrous tetrahydrofuran solution containing about 22 g of vinyl magnesium bromide with stirring and ice cooling. After the dropping stirring is continued at room temperature for 30 minutes, and thereafter the mixture is treated in a usual manner to give 12.6 g of the carbinol type compound as a colorless oil.

The so-obtained carbinol (12 g) is dissolved in 50 ml of ether, thereto is added 8.1 g of phosphorus tribromide with ice cooling, and stirring is made for 5 minutes. The reaction mixture was washed with 100 ml of cold water, the ether layer dried over anhydrous magnesium sulfate, and the ether distilled off at below 30° C. under reduced pressure. There is obtained 14 g of the cinnamyl bromide derivative as a pale yellow oil.

On the other hand, 3.0 g of moranoline is dissolved in 50 ml of ethylene glycol, 5.0 g of sodium bicarbonate then added, further the above cinnamyl bromide derivative added with stirring at room temperature over about 20 minutes, and the mixture stirred at room temperature for 3 hours. Thereafter the reaction mixture is diluted with water, acidified with hydrochloric acid, washed with ether, made alkaline with ammonia, and extracted with n-butanol. The butanol is distilled off, and the remaining crystalline substance recrystallized from a mixture of isopropyl alcohol and methanol.

Yield 4.1 g. Melting point 136°–138° C. $[\alpha]_D^{24} = -39.7°$ (methanol).

EXAMPLE 19

Synthesis of Compound 56 m-β-Methoxyethoxyacetophenone prepared from m-hydroxyacetophenone and methoxyethyl bromide is subjected to Grignard reaction as in Example 18, and the resulting carbinol compound (14.3 g) treated in 50 ml of ether with 9.2 g of phosphorus tribromide with ice cooling for 5 minutes, to give 16.4 g of the cinnamyl bromide type compound. Moranoline (3.1 g) is dissolved in 50 ml of DMSO, 5.0 g of sodium bicarbonate added, and 16 g of the bromide obtained above dropped with stirring at room temperature over 1.5 hours. After the dropping, stirring is continued for 30 minutes. Thereafter the same treatment procedure as in Example 1 follows, and the butanol extract treated with isopropyl alcohol. The resulting crystals are recrystallized from ethanol. Yield 3.13 g. Melting point 116°–119° C. $[\alpha]_D^{24} = -34.9°$ (methanol).

EXAMPLE 20

Synthesis of Compounds 56

Using p-hydroxybenzaldehyde as starting material and proceeding as in Example 18, there is obtained 7.1 g of the bromide, which is reacted with 3.2 g of moranoline and 3.3. g of sodium bicarbonate in 30 ml of DMSO with stirring at room temperature for an hour. Thereafter the reaction mixture is treated as in Example 18, and the butanol extract obtained is recrystallized from ethanol. Yield 1.68 g. Melting point 172°–174° C. $[\alpha]_D^{24} = -48.6°$ (methanol).

Compounds 4 and 6 were prepared in the same manner as in Examples 18, 19 and 20.

Compound 4 Melting point 166°–169° C., $[\alpha]_D^{24} = -43.1°$ (methanol)

Compound 6 Melting point 118°–121°, $[\alpha]_D^{24} = -37.7°$ (methanol)

EXAMPLE 21

Synthesis of Compounds 59 and 61 p-Hydroxybenzaldehyde (20 g) is dissolved in 200 ml of DMF, 44 g of anhydrous potassium carbonate and 45 g of β-methoxyethoxymethyl cloride are added, and the mixture is stirred at room temperature for 3 hours. Dilution with water, ether extraction and distillation of the extract under reduced pressure gave 25 g of a fraction having b.p. 150°–153° C./5 mmHg. This is subjected to Grignard reaction with vinyl magnesium bromide as in Example 18, 19 or 20, the carbinol so obtained treated in ether with an equimolar amount of thionyl chloride at −10° C. for one minute, and the resulting cinnamyl chloride type compound reacted with moranoline in DMSO in the presence of sodium bicarbonate as in Example 19 and 20 giving p-β-methoxyethoxymethoxycinnamylmoranoline. Melting pont 111°–114° C.

The crystals (5.2 g) obtained above is dissolved in 50 ml of methanol, 2 ml of concentrated hydrochloric acid and 5 ml of water are added, and the mixture is refluxed for 2.5 hours. The reaction mixture is evaporated to dryness under reduced pressure, the residue washed with ether, and the insoluble matter treated with a mixture of ethanol and ethyl acetate to cause crystallization. Yield 3.1 g (p-hydroxycinnamylmoranoline hydrochloride).

Synthesis of Compound 59

The crude crystals (1.0 g) obtained above is dissolved in 30 ml of methanol containing 1.0 g of potassium hydroxide, 2 ml of ethylene oxide added, and the mixture heated in a sealed tube at 80° C. for 3 hours. The reaction mixture is evaporated to dryness under reduced pressure, and the residue dissolved in water and passed through a Dowex 50W×4 (H form) ion exchanger column. The column is washed with water, the adsorbate eluted with 50% aqueous methanol containing 1% ammonia, the eluate evaporated to dryness under reduced pressure, 0.5 g of p-toluenesulfonic acid added to the remaining pale-yellow viscous product oil, and the mixture treated with isopropyl alcohol to give crystals, which are recrystallized from ethanol. Yield 0.82 g. Melting point 131°-134° C. $[\alpha]_D^{24} = -29.6°$ (methanol).

Synthesis of Compound 61

The crude p-hydroxycinnamylmoranoline (1.0 g) previously obtained is dissolved in 30 ml of methanol, 1.0 g of potassium hydroxide added, 2 ml of glycidol then added, and the mixture refluxed for 4 hours. The reaction product is recovered by the procedure for Compound 59 and converted into the p-toluenesulfonate, which is recrystallized from isopropyl alcohol. Yield 0.81 g. Melting point 126°-130° C. $[\alpha]_D^{24} = -25.8°$.

EXAMPLE 22

Synthesis of Compound 57

Tetra-O-benzylmoranoline (5.2 g, m.p. 44°-46° C., $[\alpha]_D^{24}=38°$ (ethanol)) is dissolved in 30 ml of DMF. Anhydrous potassium carbonate (3.0 g) is added, then 3.0 g of the p-methoxyethoxycinnamyl bromide mentioned in Example 20 added with stirring, and the mixture heated and stirred at 60°-70° C. for 6 hours. After the reaction, the reaction mixture is diluted with water, acidified with diluted hydrochloric acid, washed with n-hexane, made alkaline with ammonia and extracted with benzene. The benzene is distilled off and the remaining crystalline substance treated as it is with 50 ml of 24% hydrobromic acid at 90°-95° C. for 3 hours. The mixture is evaporated to dryness under reduced pressure, and the residue dissolved in water, washed with ether, made alkaline with ammonia and extracted with n-butanol. The extract is purified by silica gel chromatography with chloroform-methanol (3:1) and recrystallized from ethanol. Yield 1.83 g. Melting point 172°-174° C. $[\alpha]_D^{24} = -48.6°$ (methanol).

What is claimed is:

1. An N-substituted moranoline of the formula

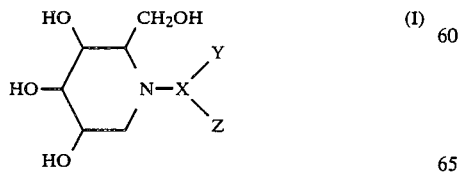

(I)

wherein X is divalent alkyl or alkenyl of 3 to 6 carbon atoms, Y is hydrogen, methyl or

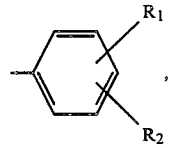

and Z is

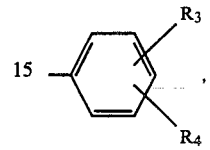

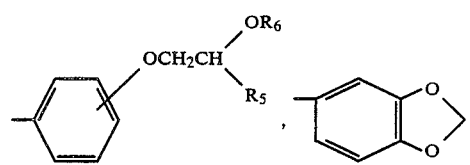

or thienyl, wherein $R_1$, $R_2$, $R_3$ and $R_4$ are independently hydrogen, halogen, lower alkyl, lower alkoxy, hydroxyl, trihalomethyl, phenoxy, diloweralkylamino, cyano, carboxyl, carbamoyl or carboloweralkoxy, $R_5$ is hydrogen or hydroxymethyl and $R_6$ is hydrogen, methyl, ethyl or methoxyethyl, or a pharmaceutically acceptable nontoxic acid addition salt thereof.

2. The moranoline derivative according to claim 1 of the formula:

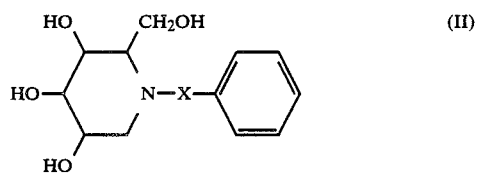

(II)

wherein X is divalent $C_3$ alkyl or $C_3$ alkenyl.

3. The moranoline derivative according to claim of the formula

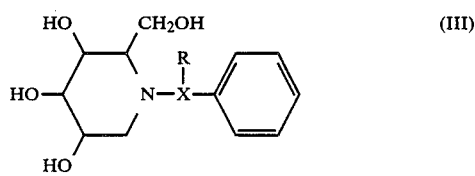

(III)

wherein R is hydrogen or phenyl and X is divalent alkyl or alkenyl of 4 or 5 carbon atoms when R is hydrogen or X is divalent alkenyl of 3, 4 or 5 carbon atoms when R is phenyl.

4. The moranoline derivative according to claim 1 of the formula

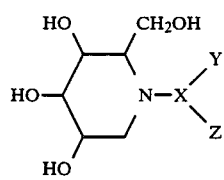
(I)

wherein X is divalent alkyl or alkenyl of 3 to 6 carbon atoms, Y is hydrogen, methyl or

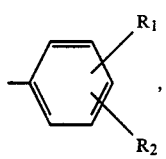

and Z is

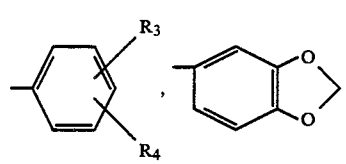

or thienyl, wherein $R_1$, $R_2$, $R_3$ and $R_4$ are independently hydrogen, halogen, lower alkyl, lower alkoxy, hydroxyl, trihalomethyl, phenoxy, diloweralkylamino, cyano, carboxyl, carbamoyl or carboloweralkoxy.

5. The moranoline derivative according to claim 1, of the formula:

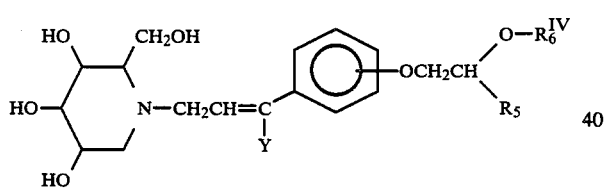

wherein Y is hydrogen or methyl, $R_5$ is hydrogen or hydroxymethyl and $R_6$ is hydrogen, methyl, ethyl or methoxyethyl.

6. The moranoline derivative according to claim 2, which is

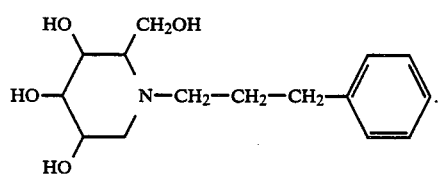

7. The moranoline derivative according to claim 2, which is

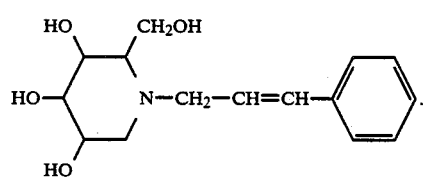

8. The moranoline derivative according to claim 3, wherein

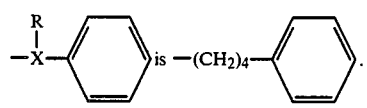

9. The moranoline derivative according to claim 3, wherein

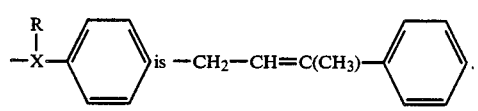

10. The moranoline derivative according to claim 3, wherein

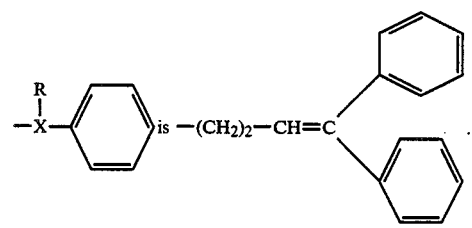

11. The moranoline derivative according to claim 3, wherein

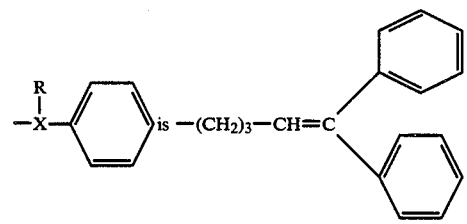

12. The moranoline derivative according to claim 3, wherein

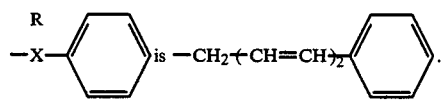

13. The moranoline derivative according to claim 4, wherein

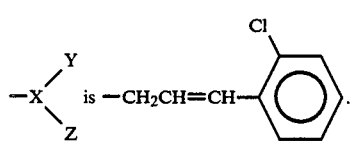

14. The moranoline derivative according to claim 4, wherein

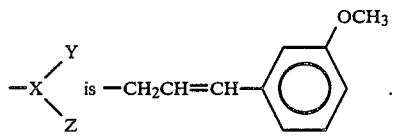

15. The moranoline derivative according to claim 4, wherein

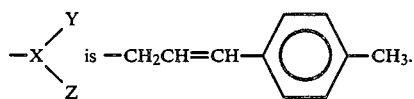

16. The moranoline derivative according to claim 4, wherein

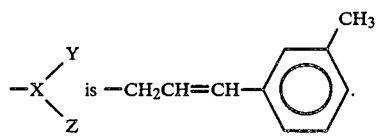

17. The moranoline derivative according to claim 4, wherein

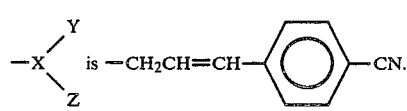

18. The moranoline derivative according to claim 4, wherein

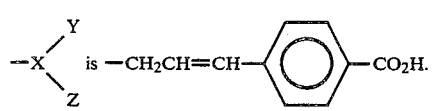

19. The moranoline derivative according to claim 4, wherein

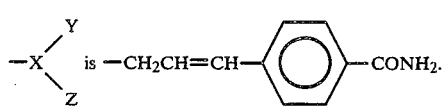

20. The moranoline derivative according to claim 4, wherein

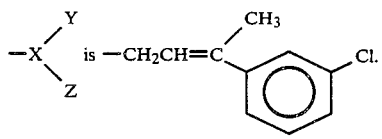

21. The moranoline derivative according to claim 4, wherein

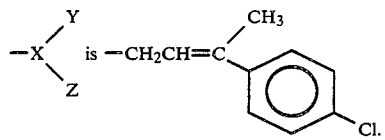

22. The moranoline derivative according to claim 4, wherein

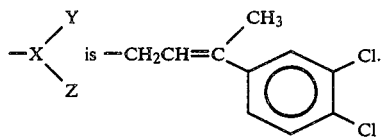

23. The moranoline derivative according to claim 4, wherein

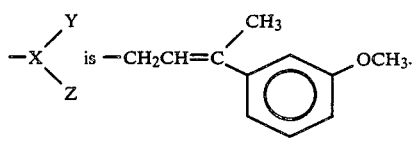

24. The moranoline derivative according to claim 4, wherein

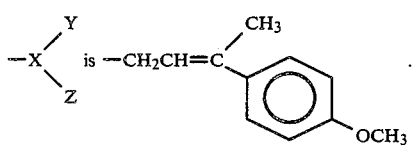

25. The moranoline derivative according to claim 4, wherein

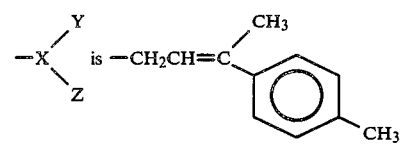

26. The moranoline derivative according to claim 4, wherein

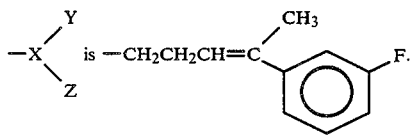

27. The moranoline derivative according to claim 4, wherein

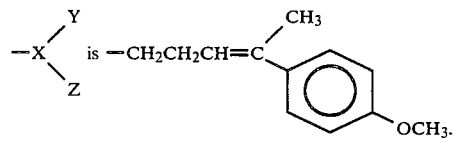

28. The moranoline derivative according to claim 4, wherein

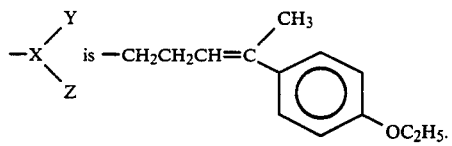

29. The moranoline derivative according to claim 4, wherein

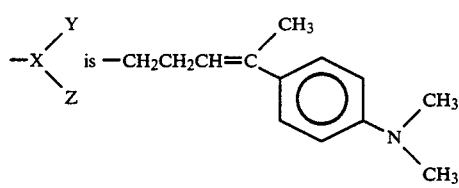

30. The moranoline derivative according to claim 4, wherein

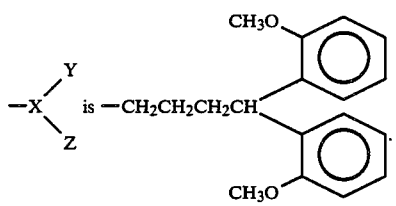

31. The moranoline derivative according to claim 4, wherein

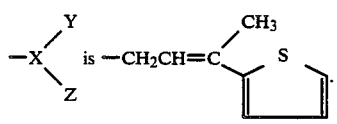

32. The moranoline derivative according to claim 5, which is

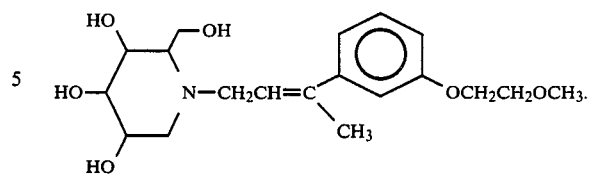

34. The moranoline derivative according to claim 5, which is

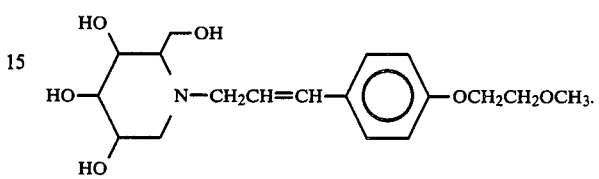

35. The moranoline derivative according to claim 5, which is

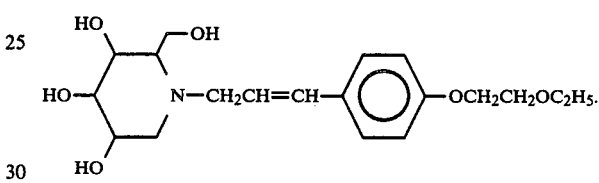

36. The moranoline derivative according to claim 5, which is

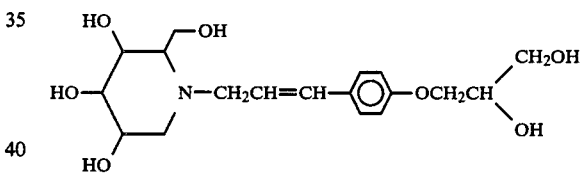

37. The moranoline derivative according to claim 5, which is

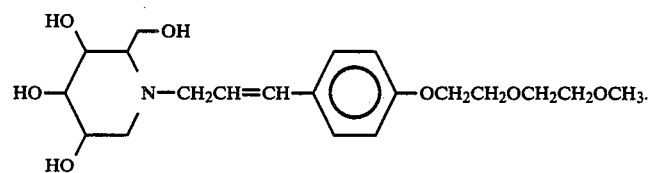

38. The moranoline derivative according to claim 5, which is

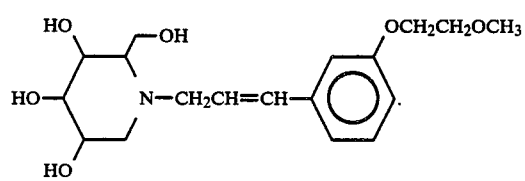

33. The moranoline derivative according to claim 5, which is

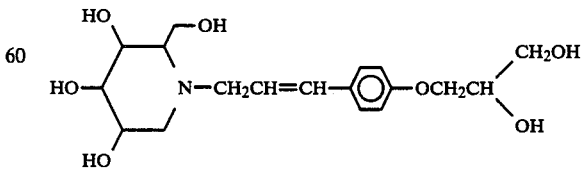

39. A composition for prophylaxis and treatment of hyperglycemic symptoms, comprising an amount of a compound of claim 1 effective to inhibit the increase of blood sugar and a pharmaceutically acceptable inert diluent carrier therefor.

40. A method for the prophylaxis or treatment of hyperglycemic symptoms, which comprises administering to a human or animal in need thereof an amount of a compound of claim 1 effective to inhibit the increase of blood sugar.

41. A compound of the formula

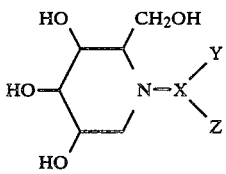

wherein X is divalent alkyl of 3 to 6 carbon atoms, Y is hydrogen or methyl and Z is

wherein $R_3$ and $R_4$ are independently hydrogen, halogen, lower alkyl, lower alkoxy, hydroxyl, trihalomethyl, diloweralkylamino, cyano, carboxyl or carboloweralkoxy, or a pharmaceutically acceptable non-toxic acid addition salt thereof.

* * * * *